(12) United States Patent
Ahari et al.

(10) Patent No.: US 11,116,812 B2
(45) Date of Patent: Sep. 14, 2021

(54) WATER-IN-OIL NANO-EMULSION OF SAFFRON AND A METHOD OF PREPARING THEREOF

(71) Applicants: Hamed Ahari, Tehran (IR); AmirAli Anvar, Tehran (IR); Mehdi Rahimian, Tehran (IR); Sara Allahyari Beik, Tehran (IR); Sima Moradi, Tehran (IR)

(72) Inventors: Hamed Ahari, Tehran (IR); AmirAli Anvar, Tehran (IR); Mehdi Rahimian, Tehran (IR); Sara Allahyari Beik, Tehran (IR); Sima Moradi, Tehran (IR)

( * ) Notice: Subject to any disclaimer, the term of this patent is extended or adjusted under 35 U.S.C. 154(b) by 0 days.

(21) Appl. No.: 17/174,340

(22) Filed: Feb. 11, 2021

(65) Prior Publication Data

US 2021/0161987 A1    Jun. 3, 2021

Related U.S. Application Data

(62) Division of application No. 17/086,763, filed on Nov. 2, 2020, now Pat. No. 10,953,065.

(51) Int. Cl.
| | | |
|---|---|---|
| *A61K 36/00* | (2006.01) | |
| *A61K 36/88* | (2006.01) | |
| *A61K 9/107* | (2006.01) | |
| *A23L 27/10* | (2016.01) | |
| *A23D 7/005* | (2006.01) | |
| *A23D 7/04* | (2006.01) | |

(52) U.S. Cl.
CPC ............ *A61K 36/88* (2013.01); *A23D 7/0053* (2013.01); *A23D 7/04* (2013.01); *A23L 27/11* (2016.08); *A61K 9/1075* (2013.01); *A23V 2002/00* (2013.01); *A61K 2236/333* (2013.01); *A61K 2236/39* (2013.01)

(58) Field of Classification Search
None
See application file for complete search history.

(56) References Cited

U.S. PATENT DOCUMENTS

2013/0156746 A1*  6/2013  Piraee ..................... A23L 33/15
424/94.1

* cited by examiner

*Primary Examiner* — Qiuwen Mi
(74) *Attorney, Agent, or Firm* — Barry Choobin; Patent 360

(57) ABSTRACT

Disclosed is a nano-emulsion formulation of saffron and a method of preparation thereof. The method includes the steps of triturating saffron with liquid nitrogen. Preparing an ultrasonic assisted extract in a polar or non-polar solvent. Preparing a nano-emulsion using the extract and one or more surfactants, including tween and span.

2 Claims, 5 Drawing Sheets

WATER-IN-OIL NANO-EMULSION OF SAFFRON AND A METHOD OF PREPARING THEREOF

CROSS-REFERENCE TO RELATED APPLICATIONS

The present application is a Divisional of U.S. patent application Ser. No. 17/086,763, filed Nov. 2, 2020, the entire contents of which is incorporated herein by reference.

SPONSORSHIP STATEMENT

The present invention is partially sponsored by Islamic Azad University, Science and Research Branch, which has no rights in this patent application.

FIELD OF INVENTION

The present disclosure relates to nano-emulsions, and more particularly, the present invention relates to a nano-emulsion formulation of saffron and a method of preparation thereof.

BACKGROUND

Saffron is one of the most palatable spices, derived from the flower of Crocus sativus L., commonly known as the "saffron crocus." As a spice, saffron is used to add flavor, color, smell, and aroma to different types of foods, clothing dyes, and supplements. Besides the main use as species, saffron also has many health benefits and therapeutic properties. Saffron is known for ages having numerous usage and benefits. Many therapeutic actions of saffron have been scientifically evaluated, some of the actions include oxytocic, anti-carcinogenic, exhilarant, anti-depressant, and anti-asthmatic. Also, saffron is a medicine in many traditional systems of medicine. Saffron is known for use in rheumatism, alcohol addiction, cold, asthma, heart disease, tumor, and cancer. Saffron is a well-known antioxidant and has hypolipidemic effects.

Saffron is known to be originated mostly in Iran which is also the world's biggest producer of saffron owning 90% of global production. The species Crocus sativus L. belongs to the family Iridaceae, crocus genus, and crocus species. It is a triploid plant with contractile roots, three stigmas, yellow anthers, and purple petals. The comparatively bitter taste and iodoform-like fragrancy of saffron come from the major phytochemicals picrocrocin and safranal. The golden-yellow hue of saffron is related to crocin, a carotenoid pigment. There are about 150 compounds in saffron among which picrocrocin and apocarotenoid compounds, such as crocetin, crocin, safranal, which are the bio-oxidative segmentation products of zeaxanthin, are considered as the most bioactive ingredients. The antibacterial and antifungal activities of Saffron and its byproducts have also brought many achievements for researchers and scientists. Safranal and picrocrocin inhibitory and bactericidal concentrations cause the antibacterial activities of Saffron which expand the horizon of both food and medicine science.

Considering the large market of saffron and its potential medical uses, serious competition over its bountiful markets has led many corporations to study and invest in other parts and byproducts of this Red Gold. Despite being of extraordinary therapeutic and commercial standing, no significant researches are available that focuses on enhancing the properties of saffron or developing better formulation and extracts A U.S. Pat. No. 7,070,823 filed Dec. 31, 2002 granted to CSIR discloses a method for the extraction of high stability, superior quality, value added, standardized, ready-to-use saffron pigments and flavor concentrate. The process includes steps of mixing saffron with one food-grade solvent or a combination of more than one food graded-solvents, macerating and agitating the mixture with continuance protection from light condition, centrifuging the macerated mixture to remove undesirable fibrous plant material, cooling the centrifuge immediately, lyophilizing the cooled centrifuge under reduced pressure to obtain crude material, isolating the concentrate by column chromatography, and obtaining brilliant orange color shining saffron pigments and flavor concentrate with recovery of about 95%, and use of the saffron pigments and flavor concentrate of range between 0.05 to 3% in food, pharmaceutical, and allied industries for flavor, and color.

A need is always appreciated for innovative methods of extraction and developing formulation that have improved properties of the active ingredients. A need is always appreciated for a formulation that has enhanced properties of saffron. A need is always appreciated for a formulation that is more effective with less amount of active ingredients.

SUMMARY OF THE INVENTION

The principal object of the present invention is therefore directed to a formulation of saffron with improved physical properties.

It is another object of the present invention that the formulation provides more intense color than saffron powder.

It is still another object of the present invention that the formulation has a richer and stronger odor.

It is yet another object of the present invention that the formulation has a more apt flavor based on the five-point hedonic scale test.

It is a further object of the present invention that the formulation has an exceptionably better flavor than the convention powder form of saffron.

It is an additional object of the present invention that the formulation is more effective overall in a small amount.

It is still an additional object of the present invention that the formulation reduces wastage, thus making the formulation more economical.

It is still a further object of the present invention that the formulation is economical to manufacture.

It is yet a further object of the present invention that the formulation has a longer shelf life.

In one aspect, disclosed is a nano-emulsion formulation of saffron and a method of preparation thereof. The method includes the steps of preparing an ultrasonic-assisted extract of saffron. For preparing the extract, first, saffron can be triturated in liquid nitrogen. Nano-emulsion can then be prepared using the extract.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The accompanying figures, which are incorporated herein, form part of the specification and illustrate embodiments of the present invention. Together with the description, the figures further explain the principles of the present invention and to enable a person skilled in the relevant arts to make and use the invention.

DETAILED DESCRIPTION

Figure 1:
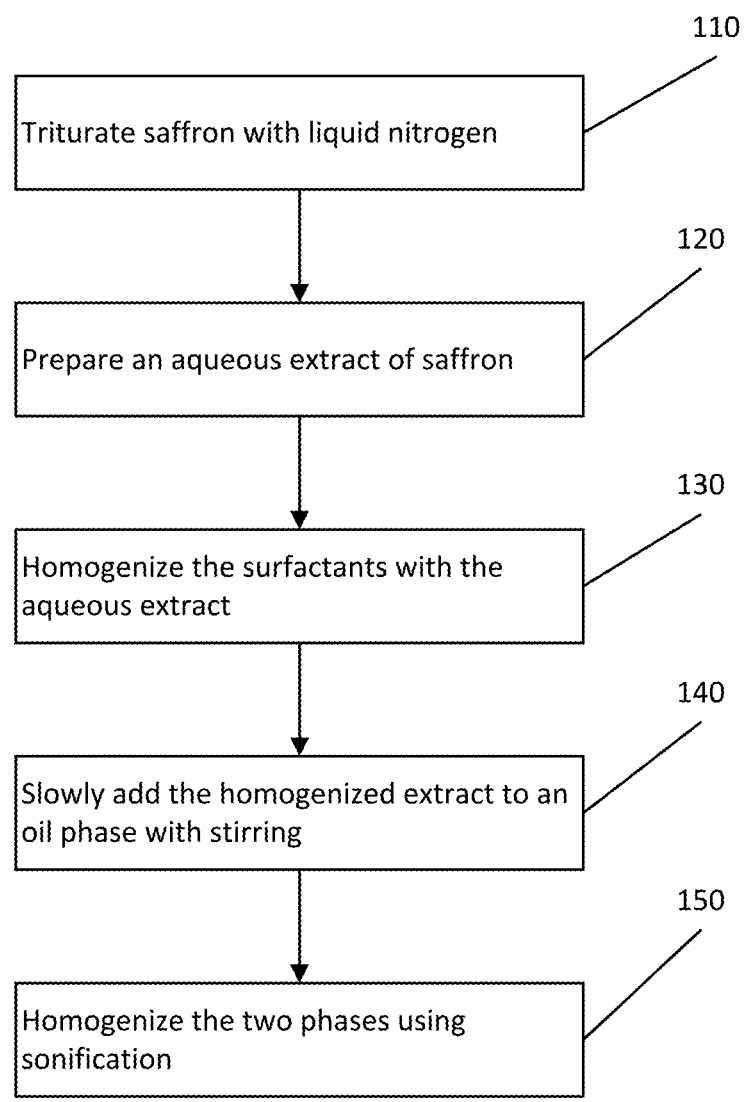
FIG. 1 is a flow chart illustrating the disclosed method of preparing the mamo-emulsion formulation of saffron, according to an exemplary embodiment of the present invention.

Subject matter will now be described more fully hereinafter. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, the reasonably broad scope for claimed or covered subject matter is intended. Among other things, for example, the subject matter may be embodied as apparatus and methods of use thereof. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is for the purpose of describing particular embodiments only and is not intended to be limiting of embodiments of the invention. As used herein, the singular forms "a", "an" and "the" are intended to include the plural forms as well, unless the context clearly indicates otherwise. It will be further understood that the terms "comprises", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely for the purpose of illustrating the general principles of the invention since the scope of the invention will be best defined by the allowed claims of any resulting patent.

The following detailed description is described with reference to the drawings, wherein like reference numerals are used to refer to like elements throughout. In the following description, for purposes of explanation, specific details may be set forth in order to provide a thorough understanding of the subject innovation. It may be evident, however, that the claimed subject matter may be practiced without these specific details. In other instances, well-known structures and apparatus are shown in block diagram form to facilitate describing the subject innovation.

By the phrase "high relative abundance of active compounds" it is meant that the level of active compounds including picrocrocin, safranal, and crocin are enhanced or enriched, such that the disclosed nano-emulsion has a higher relative abundance of active compounds, and in particular picrocrocin, safranal, and crocin, compared to conventional saffron powder.

Disclosed is a nano-emulsion based formulation of saffron and a method of preparation thereof. Referring to FIG. 1 which shows an embodiment of the method for preparing a nano-emulsion formulation of the saffron. First, stigmas from the saffron *crocus* flowers can be collected. The stigmas can then be triturated in liquid nitrogen to obtain the crushed stigmas, at step. The use of liquid nitrogen has multiple advantages included no left-over solvents. Moreover, the physical characteristics of the saffron including the color and flavor remain intact. Once the triturated crush is obtained, it can then be extracted using a polar solvent, at step 120. In one case the polar solvent can be water resulting in an aqueous extract of saffron. The amount of water can be adjusted to make the extract of the desired concentration. In one implementation, a 10% aqueous extract can be prepared. To prepare the nano-emulsion, the quantities of Tween 80, Sorbitan monooleate (Span 80), and the oil phase can be determined. The tween 80 can be added to the aqueous extract and homogenized to prepare a solution, at step 130. Span 80 can be added to the oil phase. The extract can then be added to the oil phase with continuous stirring. The two phases can then be homogenized using sonification at a slow space until the spontaneous emulsification completes. The above procedure results in a water-in-oil nano-emulsion. Similarly, an oil in water nano-emulsion can also be prepared by first extracting the saffron with a non-polar solvent and using water as the solvent phase.

In one exemplary embodiment, the surfactants Tween 80 and Span 80 can be used. The nano-emulsion may contain the surfactant for 2 weight percent, water for 96 weight percent, and essence for 1 weight percent. To provide hydrophile-lipophile equivalence, the different mass fraction of two surfactants can be computed using the below formulae.

$$HLB = (m_A \times HLB_A + m_B \times HLB_B / m_A + m_B) \times 100$$

$m_A$ & $m_B$: mass fraction of surfactants A and B respectively; $HLB_A$ & $HLB_B$: HLB of surfactants A and B respectively.

$$\% (A) = [100(X - HLB_B)] / [HLB_A - HLB_B]$$

$$\% (B) = 100 - \% (A)$$

For example, to prepare an emulsion with HLB=12, the required amount of Span 80 and Tween 80 are as follow:

$$\% \text{ Tween } 80 = [100(12 - 4.3)] / [15 - 4.3] = 72\%$$

$$\% \text{ Span } 80 = 100 - 72 = 28\%.$$

Exemplification of the Method of Preparing the Disclosed Nan-emulsion

Example 1

Preparation and Evaluation of Saffron Extracts

First, saffron triturate was prepared by triturating saffron stigmas in liquid nitrogen. The crushed saffron was used for extraction using a polar or a non-polar solvent.

Second, saffron was standardized for comparisons. Three molecules including the picrocrocin, safranal, and crocin were examined as standards using the spectrophotometry method. The solution of 1% saffron extract was added to a beaker thoroughly as the first step, then the beaker was placed on a stirrer for 1 hour at room temperature. 0.5 ml of this solution was transferred to a volumetric flask (with the capacity of 100 ml) and brought up to the volume by water. The flask plastic stopper was put on and mixed thoroughly until a monotonic solution was obtained. Distilled water was used as a control sample and spectrophotometer regulator. Thereafter, the solution was cast into the spectrophotometer cuvettes with the light transparency length of 1 cm. Subsequently, the absorbance at the wavelength spectrum of 200-700 nm was read. Acceptable standards for the saffron solution are shown in Table 1. The amount of picrocrocin, safranal, and crocin in 1 ml of a sample obtained from the main solution is procured through the following formula:

$$E_{1\,m}^{\%1} c \frac{A100}{V}$$

in which:
A: absorbance of one of the molecules mentioned above;
V: sample volume based on ml
$E^{\%\,1}$ cm: absorbance of intended factor

TABLE 1

Acceptable standards for the saffron

| Row | Characteristics | Permissible Limits | Examination Procedures |
|---|---|---|---|
| 1 | Picrocrocin (maximum absorbance at the wavelength of 257 nm) | 70-100 | Categories according to ISO/TS 3632-2 |
| 2 | Safranal (maximum absorbance at the wavelength of 330 nm) | 20-60 | Categories according to ISO/TS 3632-2 |
| 3 | Crocin (maximum absorbance at the wavelength of 440 nm) | Minimum 100 | Categories according to ISO/TS 3632-2 |
| 4 | Additive dyes | Negative | Categories according to ISO/TS 3632-2 |

Evaluation of Saffron Extracts

Figure 2A:
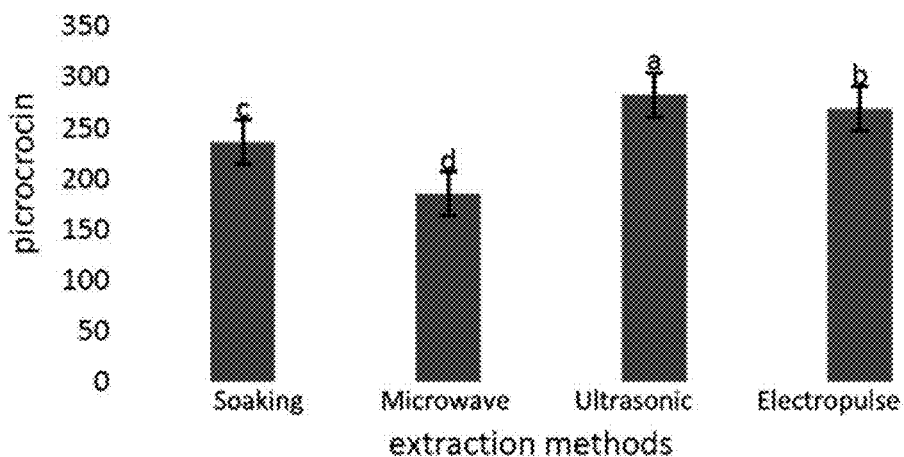
FIG. 2A shows the comparison of extraction methods affecting picrocrocin efficiency.

Results of the present study indicated that in the extraction of picrocrocin pigment, the ultrasonic method showed higher efficiency (p≤0.05). The lowest extraction efficiency was found in the microwave method (p≤0.05). FIG. 2A shows the comparison of extraction methods affecting picrocrocin efficiency. The ultrasonic method resulted in the highest concentration of picrocrocin, followed by electropulse, soaking, and microwave in the descending order.

Figure 2B:
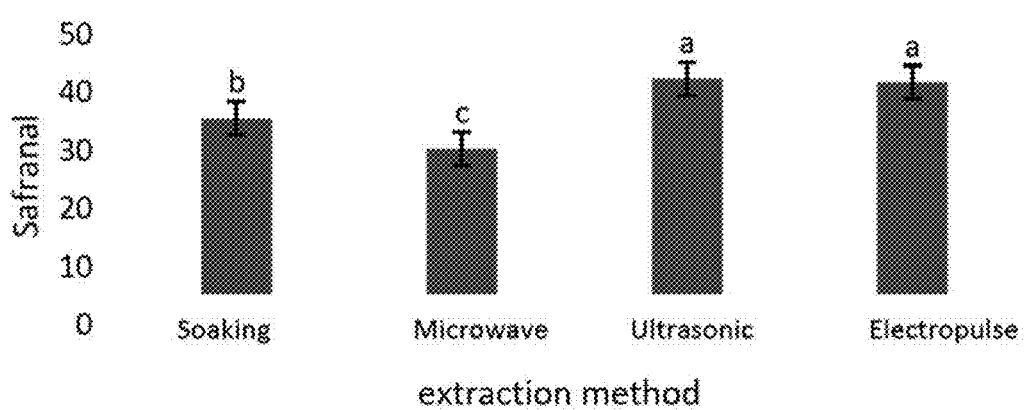
FIG. 2B shows the comparison of extraction methods affecting safranal efficiency.

Regarding safranal, similar results were obtained from the study i.e. in extraction of safranal pigments, ultrasonic method was more efficient (p≤0.05). Minimum efficiency in safranal extraction was observed in microwave method (p≤0.05). FIG. 2B shows the methods ultrasonic, and electropulse resulting in the same concentration. Soaking method resulted in lesser concentration, while the microwave method produced lowest concentration of the safranal in the extract.

Figure 2C:
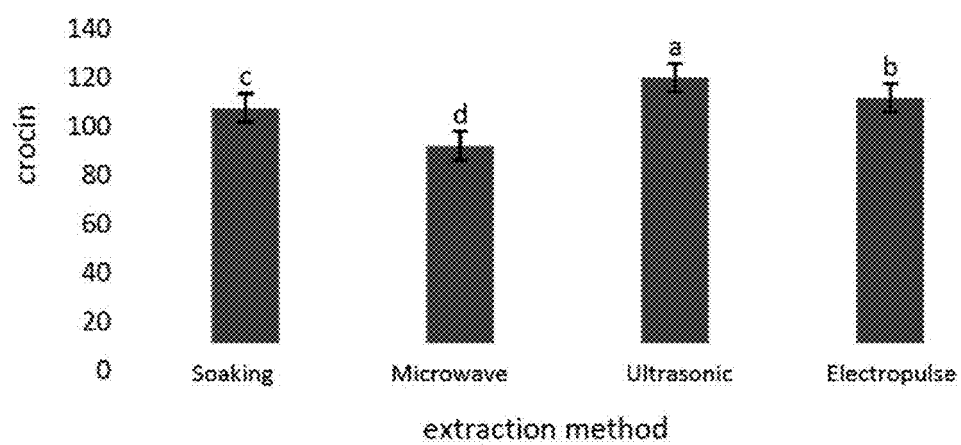
FIG. 2C shows the comparison of extraction methods affecting crocin efficiency.

Regarding crocin, the results of this study showed that in extraction of crocin pigments, ultrasonic method had more efficiency (p≤0.05). minimum efficiency in crocin extraction was observed in microwave method (p≤0.05). FIG. 2C shows that the ultrasonic method resulting in maximum concentration of crocin followed by electropulse, soaking, and microwave. Thus, ultrasonic assisted extraction results in a high relative abundance of active compounds.

Example 2

Preparation and Evaluation of Nano-Emulsions

Method (1): Preparation of Spontaneous Nano-Emulsification (W/O)

Surfactant combination of HLB value "4" was prepared having the below compositions:

[Tween20+Span80]: % Tween=5.645161, % Span=94.35484, or

[Tween80+Span80]: % Tween=6.542056, % Span=93.45794.

TABLE 2

Water-in-oil spontaneous nano-emulsification (method 1)

| Contents | Amount (%) |
|---|---|
| Saffron aqueous extract (10%) | 5 |
| Tween 80 | 2.29 |
| Sorbitan monooleate (span80) | 33 |
| Sunflower oil | 65 |

Tween 80 in the amount shown in Table 2 was added to the 10% Saffron aqueous extract with stirring. Separately, Span 80 was added to the sunflower oil with stirring. Thereafter, the aqueous phase was slowly added to the oil phase with continuous stirring. The mixture was homogenized using ultrasonic energy at a slow pace until the spontaneous emulsification was completed.

Method 2: PIT Nano-Emulsification (Phase Inversion Temperature) (O/W)

Oil in water nano-emulsion was prepared using the surfactant combination of HLB value "10".

TABLE 3

PIT nano-emulsification (method 2)

| Contents | Percentage (%) |
|---|---|
| n-Decane saffron extraction (10%) | 10 |
| Span 80 | 2 |
| Maltodextrin | 1 |
| Water | 80 |
| Glycerol | 5 |
| Tween 20 | 2 |

Glycerol was used with Tween 20 as co-emulsifier. Water was used at 4° C. All the components were takes in quantities as shown in Table 3. Tween 20, Glycerol, and Maltodextrin were mixed in water to form an aqueous phase. Span 80 was mixed in the extract to form the oil phase. The oil phase was added to the aqueous phase with continues stirring. First a high-speed homogenizer was used to homogenize the two phases. Thereafter, the emulsion was further homogenized using an ultrasonic homogenizer.

Method 3: Spontaneous Nano-Emulsification (W/O)

Water in oil nano-emulsion was prepared using the surfactant combination of HLB value "4".

TABLE 4

| Spontaneous nano-emulsification (method 3) | |
| --- | --- |
| Contents | Percentage (%) |
| Saffron aqueous extract (10%) | 10 |
| Span 80 | 44.5 |
| Olive oil | 85 |
| Tween 20 | 2.5 |

Tween 20 was used instead of Tween 80. Using the components shown in Table 4, the method 1 was followed for the preparation of the nano-emulsion.

Method 4: PIT Nano-Emulsification (Phase Inversion Temperature) (O/W)

Oil in water nano-emulsion was prepared using the surfactant combination of HLB value "10".

TABLE 5

| PIT nano-emulsification (method 4) | |
| --- | --- |
| Contents | Percentage (%) |
| n-Decane saffron extraction (10%) | 10 |
| Span 80 | 2.5 |
| Maltodextrin | 1 |
| Water | 85 |
| Tween 20 | 2.5 |
| Dry Ice | — |

All the components were takes in quantities as shown in the Table 5. Tween 20 and Maltodextrin were mixed in water to form an aqueous phase. Spa 80 was mixed in the extract to form the oil phase. The oil phase was added to the aqueous phase with continues stirring. First a high-speed homogenizer was used to homogenize the two phases. Thereafter, the emulsion was further homogenized using an ultrasonic homogenizer. Homogenization was done with dry ice of low temperature of about 4° C. around the nano-emulsion plate for homogenization.

Determination of the Stability of the Nano-Emulsions Prepared Using the Above Methods (1)-(4).

The produced nano-emulsions were qualified for ten days at room temperature (for further changes in a short time). The study criteria were the stability of the three molecules: picrocrocin, safranal and crocin.

Figure 3A:
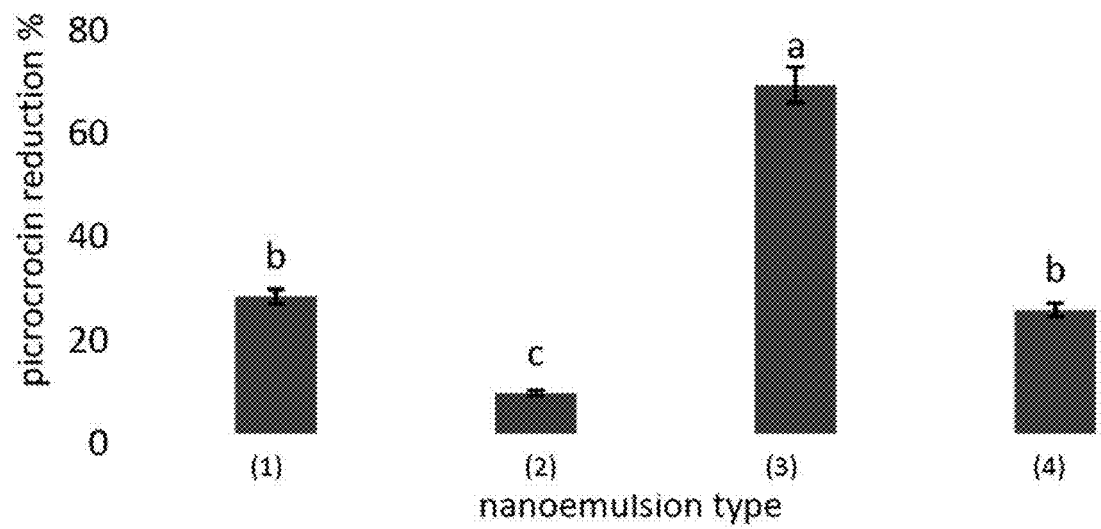
FIG. 3A shows the percentage reduction of picrocrocin based on the type of nano-emulsion.

Referring to FIG. 3A, the study revealed that in method 3, the rate of picrocrocin reduction increased significantly ($p \leq 0.05$). The minimum rate of picrocrocin reduction was observed in method 2 ($p \leq 0.05$).

Figure 3B:
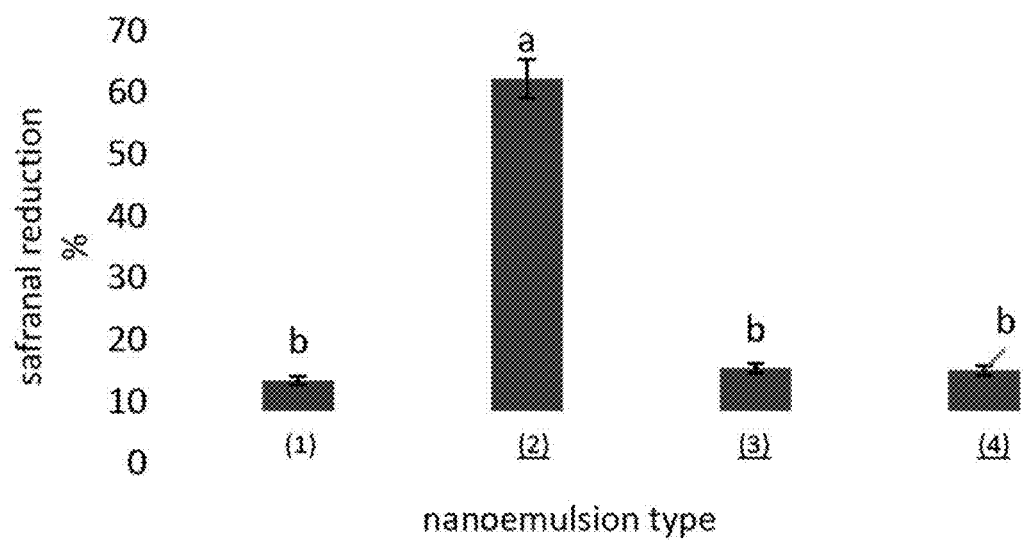
FIG. 3B shows the percentage reduction of safranal based on the type of nano-emulsion.

Referring to FIG. 3B, the study revealed that the rate of safranal reduction significantly grew trough method 2 ($p \leq 0.05$).

Figure 3C:
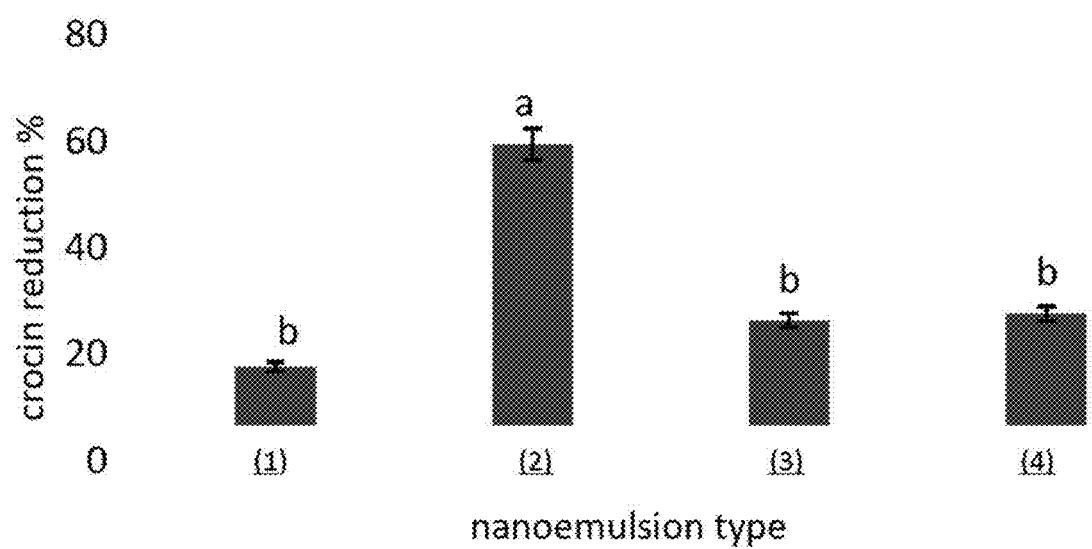
FIG. 3C shows the percentage reduction of crocin based on the type of nano-emulsion.

Referring to FIG. 3C, the study revealed that the of crocin reduction increased significantly through method 2 ($p \leq 0.05$).

What is claimed is:

1. A method of preparing a nano-emulsion of saffron, the method comprising the steps of:
   triturating stigmas of saffron in liquid nitrogen to obtain crushed saffron;
   preparing an ultrasonic-assisted extract of the crushed saffron in an aqueous solvent;
   adding sorbitan monooleate in olive oil to obtain an oil phase;
   adding polyoxyethylene (20) sorbitan monolaurate to the extract to obtain an aqueous phase;
   slowly adding the aqueous phase to the oil phase with continuous stirring to form a mixture; and
   subjecting the mixture to a high-speed homogenizer followed by an ultrasonic homogenizer to obtain a water-in-oil nano-emulsion.

2. The method according to claim 1, wherein the extract is of 10% crushed saffron in aqueous solvent, and components are added in the following proportions:
   extract—10%
   sorbitan monooleate 80—2.5%
   Olive oil—85%, and
   polyoxyethylene (20) sorbitan monolaurate—2.5%.

* * * * *